United States Patent [19]

Brugger et al.

[11] Patent Number: 5,650,071

[45] Date of Patent: Jul. 22, 1997

[54] TECHNIQUE FOR PRIMING AND RECIRCULATING FLUID THROUGH A DIALYSIS MACHINE TO PREPARE THE MACHINE FOR USE

[75] Inventors: James Brugger, Boulder; Dan Lee Hendrickson, Golden; Roy Sven Hovland, Denver, all of Colo.

[73] Assignee: COBE Laboratories, Inc., Lakewood, Colo.

[21] Appl. No.: 481,755

[22] Filed: Jun. 7, 1995

[51] Int. Cl.[6] .......................... A61M 37/00; B01D 11/00; B01D 61/00; C02F 1/44

[52] U.S. Cl. .................................... 210/646; 604/4

[58] Field of Search ................... 604/4, 5, 6, 28, 604/29; 210/646

[56] References Cited

U.S. PATENT DOCUMENTS

| | | | |
|---|---|---|---|
| 4,107,039 | 8/1978 | Lindsay, Jr. et al. | 210/90 |
| 4,209,391 | 6/1980 | Lipps et al. | 210/22 A |
| 4,293,413 | 10/1981 | Schnell | 210/188 |
| 4,334,988 | 6/1982 | Milligan | 210/87 |
| 5,041,215 | 8/1991 | Chamberlain, Jr. et al. | 210/136 |
| 5,141,493 | 8/1992 | Jacobsen et al. | 604/28 |
| 5,498,338 | 3/1996 | Kruger et al. | 210/641 |

FOREIGN PATENT DOCUMENTS

| | | |
|---|---|---|
| 8106491 | 10/1981 | Germany. |
| WO88/06460 | 9/1988 | WIPO. |

*Primary Examiner*—John G. Weiss
*Assistant Examiner*—Ki Yong O
*Attorney, Agent, or Firm*—John B. Phillips

[57] ABSTRACT

A technique for automatically priming and recirculating sterile fluid through an extracorporeal circuit of a dialysis machine having a blood pump, a dialyzer, and a blood tubing set including an arterial line for drawing blood from a patient and a venous line for returning the blood to the patient. The dialysis machine selectively opens and closes clamps on the arterial and venous lines and further operates a waste valve for selectively opening and closing a waste line leading to a waste drain. A connector attaches both the arterial and venous lines to the waste line downstream of the arterial and venous clamps and upstream of the waste valve. The dialysis machine automatically operating the blood pump, the clamps and the waste valve to flush the dialyzer and the blood tubing set with the sterile fluid and direct the used fluid down the waste drain. The dialysis machine then operating the blood pump and the clamps to again fill the dialyzer and the blood tubing set with additional sterile fluid and recirculate the sterile fluid through the extracorporeal circuit without the assistance of a dialysis machine operator. The dialysis machine further providing the operator with an indication when the recirculation process is complete. The connector being either one component of the disposable blood tubing set or a permanent component fixed to the dialysis machine.

31 Claims, 9 Drawing Sheets

TECHNIQUE FOR PRIMING AND RECIRCULATING FLUID THROUGH A DIALYSIS MACHINE TO PREPARE THE MACHINE FOR USE

The present invention relates to a new and improved dialysis system and technique for automatically priming and recirculating fluid through a dialyzer and a disposable blood tubing set which connects a patient to a dialysis machine.

CROSS REFERENCE TO RELATED INVENTIONS

This invention is related to the inventions described in U.S. patent applications for Technique for Using a Dialysis Machine to Disinfect a Blood Tubing Set, Ser. No. 08/481,754 and Technique For Automatically Preparing a Dialysis Machine at a Predetermined Date and Time, Ser. No. 08/481,754 both of which were filed concurrently therewith. Both of these applications are assigned to the assignee hereof. The disclosures of these applications are further incorporated herein by this reference.

BACKGROUND OF THE INVENTION

A dialysis system is used as a substitute for the natural kidney functions of a human body. The dialysis system cleans the blood of the natural accumulation of bodily wastes by separating the wastes from the blood outside or extracorporeally of the body. The separated wastes are discharged and the cleansed blood is returned to the body.

The dialysis system consists of a dialysis machine, a dialyzer, a disposable blood tubing set and a supply of chemicals for producing a dialysate solution used within the dialyzer. The dialyzer is used with the dialysis machine to separate the wastes from the blood. The dialyzer includes a porous membrane located within a closed housing which effectively separates the housing into a blood compartment and a dialysate or filtrate compartment. The blood removed from the patient flows through the disposable blood tubing set and the blood side of the dialyzer. The dialysate solution prepared from the chemicals is passed through the dialysate side of the dialyzer. The wastes from the blood pass through the membrane by osmosis, ionic transfer or fluid transport into the dialysate and, depending upon the type of dialysis treatment, desirable components from the dialysate may pass in the opposite direction through the membrane and into the blood. The transfer of the wastes into the dialysate cleanses the blood while allowing the desired components from the dialysate to enter the bloodstream.

The transfer of blood between the patient and the dialyzer occurs within a disposable blood tubing set. The blood tubing set and the dialyzer represent a closed extracorporeal path through which the patient's blood travels. The blood tubing set includes an arterial line connected to an arterial reservoir for drawing blood from a patient, a venous line connected to a venous reservoir for returning blood to the patient, and a number of other lines for connecting a pump and the dialyzer between the arterial and venous reservoirs. Before the blood tubing set and the dialyzer can be used in a dialysis treatment, both must be primed with a sterile saline solution to remove air from the extracorporeal circuit. Once primed, the saline solution is recirculated through the blood tubing set and the dialyzer to produce a stabilized flow and remove additional trapped air from within the extracorporeal circuit. The priming and recirculating process also serves to clean the dialyzer and flush the dialyzer membrane of any debris or chemicals remaining from a prior use.

If a patient reuses the same dialyzer for subsequent dialysis treatments, that dialyzer must be cleaned with a disinfectant or sterilant solution. However, the sterilant itself must be cleaned from the dialyzer prior to each dialysis treatment. Such a cleaning procedure effectively takes place when the dialyzer undergoes the priming and recirculating process discussed above. During priming, the dialyzer is flushed with saline solution which removes a majority of the sterilant. Additionally, during recirculation of the saline solution, the dialysis machine can be commanded to remove or "pull" a predetermined flow of saline directly from the dialyzer. This predetermined flow corresponds to "pulling off" a predetermined amount of fluid (or weight) from a patient during dialysis, and is commonly referred to as "ultrafiltration." Removing saline by ultrafiltration during recirculation of the saline solution thus allows the remaining sterilant within the dialyzer to be removed as it mixes with the saline. The saline that is removed by ultrafiltration is replenished from a saline source connected to the extracorporeal circuit so that no additional air is added to the extracorporeal circuit during recirculation.

Current dialysis machines require that the priming and recirculation steps be undertaken separately, and further require an operator to alter the configuration of the blood tubing set and the saline source upon the conclusion of the priming step and before the start of the recirculation step. For example, a typical priming sequence on a conventional dialysis machine requires that the operator connect the outlet of the dialysis machine (i.e., the venous line) to a saline source and then operate the dialysis machine in reverse to fill the extracorporeal circuit with saline. Initially, the priming solution passes through the dialyzer and, in light of the reverse flow, exits the extracorporeal circuit through the dialysis machine's input line (i.e., the arterial line) which the operator connects to a waste basin or drain to dispose of the priming solution. The initial priming solution is discarded because it may contain relatively large quantities of sterilant flushed from the dialyzer when the dialyzer is sterilized and reused following a previous dialysis treatment.

Once the blood tubing set and dialyzer have been primed, the operator must disconnect the venous and arterial lines of the blood tubing set from the saline source and waste basin, respectively, and then connect the venous and arterial lines together (i.e., short circuiting the patient). The operator then switches the dialysis machine from its reverse operation and operates the machine normally to recirculate the saline solution through the extracorporeal circuit. The operator must further connect the saline source to a different portion of the circuit so that additional saline may be supplied to replace the saline removed by ultrafiltration during recirculation.

Thus, the processes of priming and recirculating conventional dialysis machines requires significant attention from a trained operator. The operator must configure the machine at several points during the process. Of the two separate procedures, recirculating the saline requires more time than initially priming the circuit with saline. Thus, if the operator is distracted after beginning the priming procedure and is unable to immediately return to the machine to reconfigure the blood tubing set and begin the recirculation procedure, a significant delay may be experienced in preparing the machine for the next patient. The potential for delay is significantly increased in a hospital or clinical setting where an operator or nurse must set up a number of different dialysis machines over the course of a day and where there is a greater possibility of distraction.

Additionally, while a skilled nurse or technician would be unlikely to make a mistake during the set up of a dialysis machine, the often hectic atmosphere of a hospital or clinic increases the chances of an error in machine set-up. For example, an operator may become distracted while the dialysis machine is recirculating and pulling saline from the dialyzer. If the saline source (e.g., a typical saline bag) were to run dry while the operator was distracted, the machine would continue to pull saline through the dialyzer and would tend to empty the extracorporeal circuit of saline, thereby allowing air to enter the circuit. Once a significant amount of air is introduced into the circuit, the priming and recirculation process must be started over at the cost of machine down-time and a new bag of sterile saline solution. Furthermore, although hospitals and dialysis clinics typically establish specific parameters for the set up and use of dialysis machines, these specific parameters may not be adhered to by an operator when setting up a particular dialysis machine. For example, inconsistent priming or recirculation procedures (such as too little saline during priming or running the machine for too short a time during recirculation) may be followed when the operator is distracted during the course of setting up the dialysis machine or when a hospital or clinic hires a new operator that is unfamiliar with the established set-up parameters.

These and other considerations have contributed to the evolution of the present invention which is summarized below.

SUMMARY OF THE INVENTION

One of the significant aspects of the present invention pertains to a new method of priming and recirculating sterile fluid through an extracorporeal circuit of a dialysis machine without requiring that a dialysis machine operator modify the configuration of the dialysis machine between the separate steps of priming and recirculating. Another significant aspect of the present invention relates to freeing a dialysis machine operator to attend other duties while the dialysis machine automatically primes and recirculates sterile fluid through the extracorporeal circuit prior to connecting the dialysis machine to a patient. A further significant aspect of the present invention relates to providing a method of priming and recirculating a dialysis machine which consistently follows specific priming and recirculation parameters established by a hospital or clinic, and which is not subject to human error after the priming and recirculating process has been initiated. A further significant aspect of the present invention relates to conserving the sterile solution used to prime the extracorporeal circuit and which is recirculated through the circuit after the circuit has been initially primed.

In accordance with these and other aspects, the present invention may be generally summarized as a method of setting up a dialysis machine having a blood pump, a dialyzer, and a blood tubing set which includes an arterial line for drawing blood from a patient, an arterial reservoir for storing the blood received from the patient, a venous reservoir for storing the blood pumped from the arterial reservoir through the dialyzer, and a venous line for returning the blood from the venous reservoir to the patient. The dialysis machine incorporating the present invention further includes a connector adapted to connect the arterial line and the venous line to a waste line leading to a waste drain, and a waste valve positioned along the waste line between the connector and the waste drain. The connector is preferably one element of the disposable blood tubing set.

The waste valve may be selectively opened and closed to drain fluid from either the arterial line or the venous line (when the waste valve is opened) and to transfer fluid between the arterial and venous lines through the connector (when the waste valve is closed). By selectively operating the blood pump and the waste valve, in addition to clamps attached to both the arterial and the venous lines, the dialysis machine can automatically complete both the priming and the recirculation procedure without the assistance of the dialysis machine operator. The operator is required to connect a source of sterile fluid (e.g., a saline bag) to the blood tubing set, and connect the arterial and venous lines to the waste line via the connector, before commanding the dialysis machine to begin the priming and recirculating process.

The process of priming and recirculating fluid through the extracorporeal circuit preferably includes the following steps: closing an arterial clamp on the arterial line to prevent fluid from filling the arterial line; filling the arterial reservoir with a sterile solution; opening the arterial clamp and the waste valve to fill the arterial line with sterile solution from the arterial reservoir and to allow some amount of the sterile solution within the arterial line to drain through the connector and down the waste drain past the open waste valve; closing the arterial clamp to preserve the sterile solution within the arterial line; opening a venous clamp on the venous line and running the pump in a forward direction to draw sterile solution from the arterial reservoir through the dialyzer and the venous reservoir and to allow the sterile solution to drain through the venous line and the connector and down the waste drain past the open waste valve; closing the waste valve, opening the arterial clamp and running the pump backwards to circulate the sterile solution backwards through the dialyzer and the blood tubing set to remove air from the dialyzer; and running the pump forward to recirculate the sterile solution through the dialyzer and the blood tubing set.

Additional steps may be added to the basic sequence of steps noted above. For example, fluid may be drawn directly from the dialyzer while the sterile solution is being recirculated through the dialyzer and the blood tubing set.

The above steps are preferably controlled automatically by the dialysis machine, although one or more of the initial steps may be performed manually by the dialysis machine operator while still remaining within the scope of the present invention. The substantially automatic control of the priming and recirculating process both frees the dialysis machine operator to attend to other responsibilities and reduces the potential for errors by the operator. Additionally, the automatic nature of the set-up process provides a consistently prepared dialysis machine and typically utilizes less sterile saline solution than manual priming and recirculation procedures.

A more complete appreciation of the present invention and its scope may be obtained from the accompanying drawings, which are briefly summarized below, from the following detailed descriptions of presently preferred embodiments of the invention, and from the appended claims.

DETAILED DESCRIPTION

Figure 1:
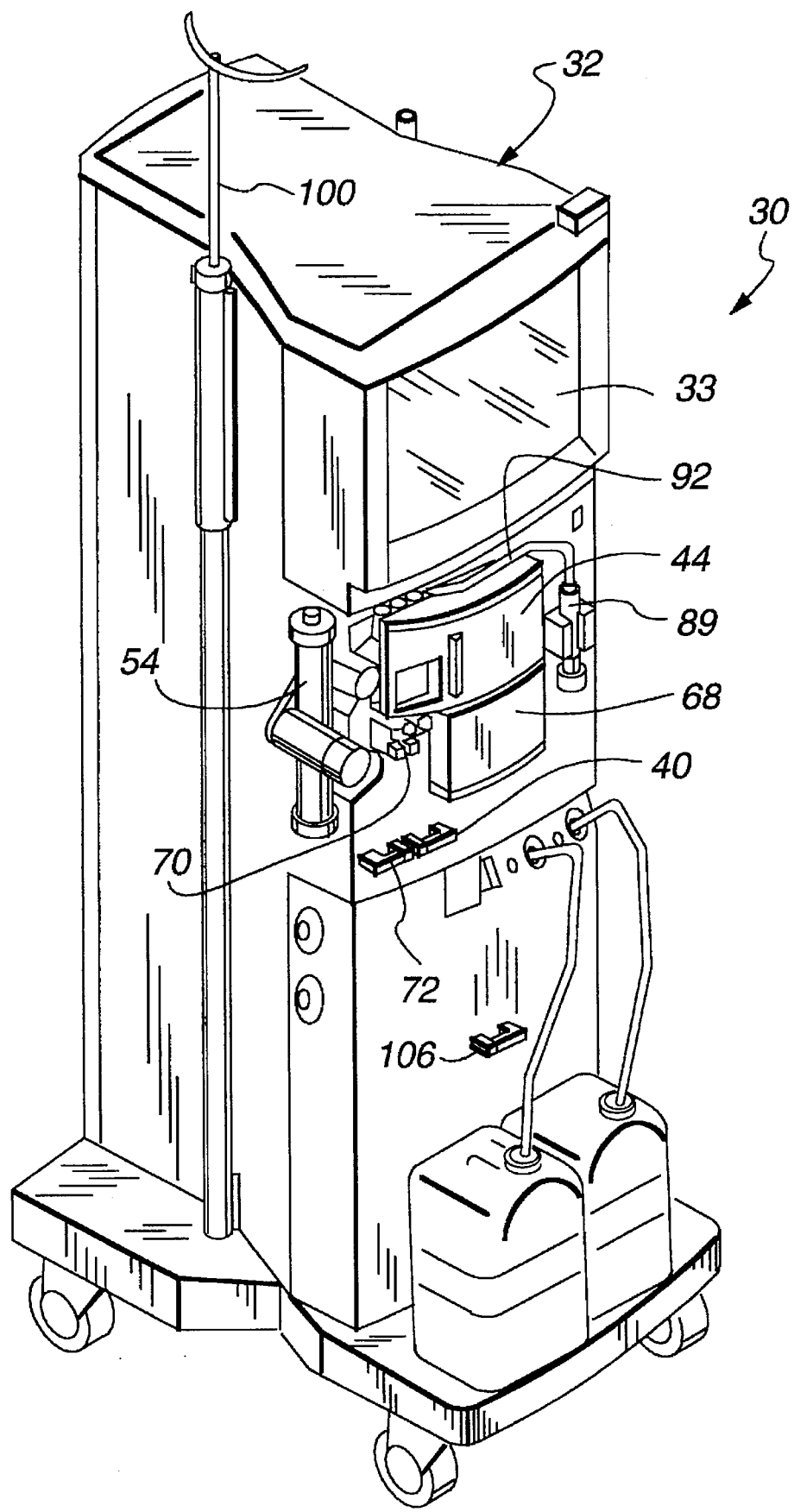
FIG. 1 is a perspective view of a dialysis machine which incorporates the present invention.
Figure 2:
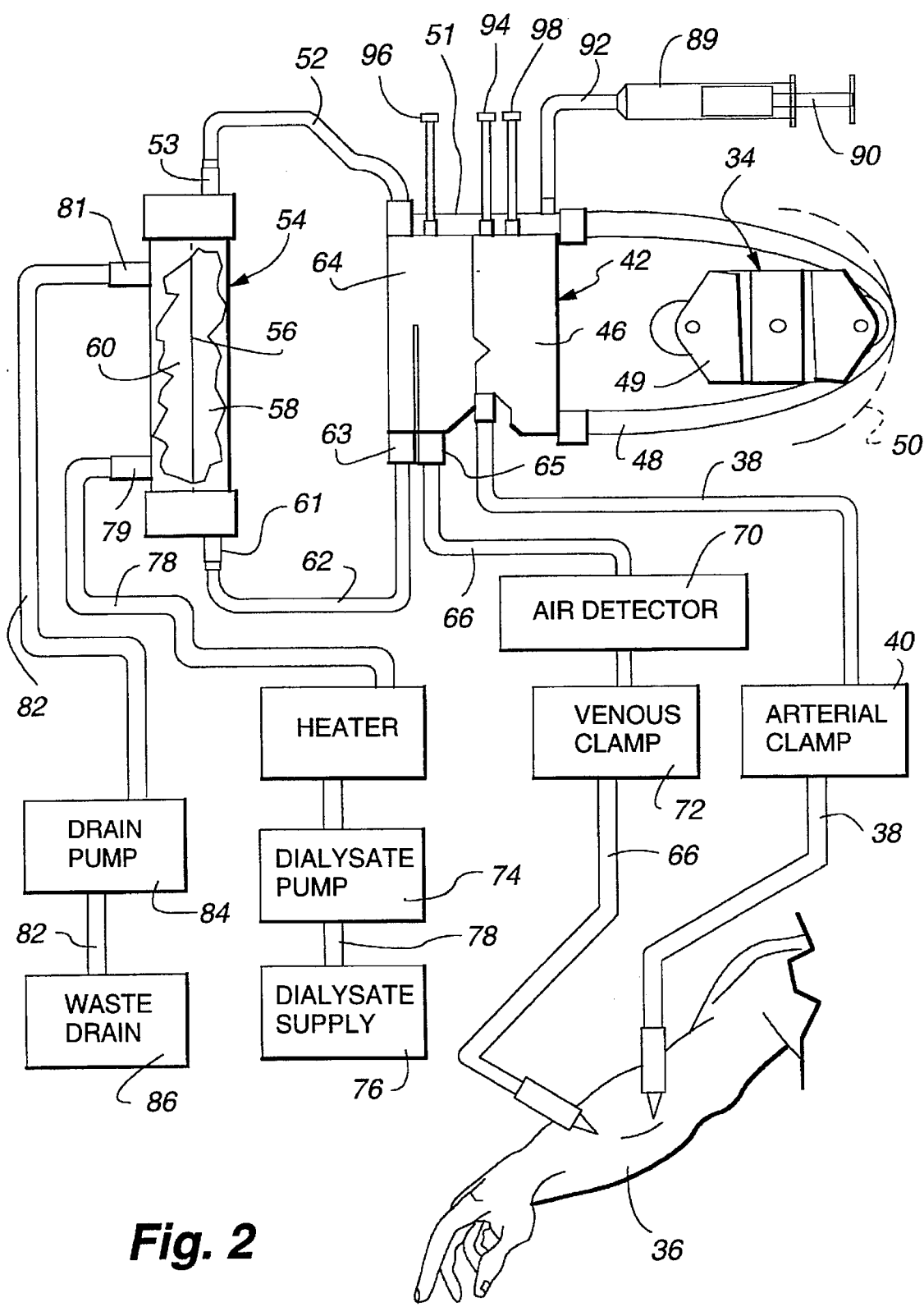
FIG. 2 is a generalized view illustrating a dialyzer, an extracorporeal blood flow path from a patient through the dialyzer, and a dialysate flow path through the dialyzer, as are present during treatment of a patient with the dialysis machine shown in FIG. 1.

An example of a dialysis machine with which the present invention may be advantageously employed is shown at 30 in FIG. 1. The dialysis machine 30 includes an enclosure 32 to which are attached, or within which are housed, those functional devices and components of the dialysis machine 30 which are generally illustrated in FIG. 2. The enclosure 30 also includes a conventional input/output ("I/O") device for controlling the machine 30, such as a touch-screen monitor 33 as shown in FIG. 1.

The dialysis machine 30 includes at least one blood pump 34 which controls the flow of blood from a patient 36. An arterial line or tubing 38 is connected through an arterial clamp 40 to a blood handling cartridge 42. The blood handling cartridge 42 is normally retained behind a door 44 (FIG. 1) of the machine 30 when used, thus the blood handling cartridge 42 is not shown in FIG. 1. The blood pump 34 also is located behind the door 44 adjacent to the cartridge 42. The blood pump 34 in dialysis machines is typically a peristaltic pump.

Blood from the patient 36 flows through an extracorporeal circuit when the arterial clamp 40 is open and the blood pump 34 draws blood from the patient 36. The blood passes through the arterial line 38 and into an arterial reservoir 46 of the cartridge 42. The blood pump 34 draws blood from the arterial reservoir 46 through a pump header 48 which is squeezed or pinched by a rotating rotor 49 against a stationary raceway 50, in the typical manner of peristaltic pumps. The blood within the pump header 48 which is rotationally in front of the rotor 49 is propelled through the pump header 48 and into a manifold 51 of the cartridge 42. A tubing 52 conducts the blood from the manifold 51 of the cartridge 42 into a blood inlet 53 of a conventional dialyzer 54. A micro-porous membrane or other type of dialysis medium 56 divides the interior of the dialyzer 54 into a blood chamber 58 and a dialysate chamber 60.

As the patient's blood passes through the dialyzer 54, the waste products within the blood pass through the medium 56 where they mix with the dialysate in the chamber 60. The cleansed blood then exits the dialyzer 54 through a blood outlet 61 and is then transferred through a tubing 62 to an inlet 63 of a venous reservoir 64 of the cartridge 42. Any air which might have been unintentionally introduced into the blood is collected and removed while the blood is in the venous reservoir 64.

Blood exits the venous reservoir 64 through an outlet 65 and is removed from the cartridge 42 through a venous tubing or line 66. Although not shown in FIG. 2, a venous blood pump similar to the arterial blood pump 34 may be located along the venous line 66 to assist in returning the blood to the patient 36. If employed, the venous blood pump is positioned behind a second door 68 as shown in FIG. 1.

After leaving the venous reservoir 64, the blood flows through the venous line 66 to an air detector 70. The air detector 70 derives signals related to the quantity of air, if any, remaining in the venous line. If an excessive or dangerous amount of air is present, a venous line clamp 72 will immediately close and the blood pump 34 will stop to terminate the flow of blood through the venous line 66 before the detected air reaches the patient 36.

The enclosure 32 of the dialysis machine 30 also encloses the various elements of a dialysate flow path, shown in abbreviated form in FIG. 2. The elements of the dialysate flow path include a number of different valves (most of which are not shown) and a dialysate pump 74 which draws dialysate from a container or from an internal supply 76 of dialysate which the dialysis machine 30 has prepared from appropriate chemicals and a supply of purified water.

The dialysate pump 74 draws the dialysate from the supply 76 and delivers the dialysate through a dialysate supply tubing or line 78 to an inlet 79 of the dialysate chamber 60 of the dialyzer 54. The dialysate flows past the medium 56 where it absorbs the waste products from the blood in the blood chamber 58. Any beneficial components within the dialysate which are desired to be transferred to the blood pass through the medium 56 and enter the blood in the blood chamber 58.

Dialysate containing the waste products exits the dialysate chamber 60 through an outlet 81 and is removed from the dialyzer 54 through a dialysate waste tubing or line 82 by operation of a drain pump 84. The drain pump 84 may be operated at a lesser volumetric pumping rate compared to the volumetric pumping rate of the dialysate pump 74 when it is desired to transfer components from the dialysate into the blood by fluid transport within the dialyzer 54. The drain pump 84 is operated at a greater volumetric pumping rate compared to the volumetric pumping rate of the dialysate pump 74 when it is desired to remove fluid components from the blood by fluid transport. Both of these flow control techniques are known as ultrafiltration and are well known dialysis treatments.

The dialysate removed from the dialyzer 54 is delivered through the waste tubing 82 to a waste drain 86. The waste drain 86 may be a separate container which receives the used dialysate and accumulated waste products, or it may simply be a drain to a public sewer. The various valves and pumps which control the dialysate flow path are referred to generally as the dialysate hydraulics.

Because the blood in the extracorporeal flow path is prone to clot, it is typical to inject an anticoagulant such as heparin into the extracorporeal flow path. The typical approach to injecting the anticoagulant is to slowly deliver it from a syringe 89. A plunger 90 of the syringe is slowly and controllably displaced into the syringe 89 by a linear driver mechanism (not shown), which is typically referred to as the anticoagulant pump. Anticoagulant from the syringe 89 is introduced into the manifold 51 of the cartridge 42 through a tubing 92 connected to the syringe as shown in FIG. 2. The anticoagulant pump is controlled to deliver the desired amount of anticoagulant during the dialysis treatment by the degree to which the anticoagulant pump moves the plunger 90 into the syringe 89 over a given time period.

Tubings 94 and 96 are respectively connected to the arterial reservoir 46 and venous reservoir 64 of the cartridge 42 as shown in FIG. 2. Clamps or caps (not shown) are connected to the ends of the tubings 94 and 96 to selectively vent accumulated air from the reservoirs 46 and 64. A saline tubing 98 is also connected to the arterial reservoir 46 so that saline may be directly administered to the patient during treatment in case of low blood pressure. A pole 100 for supporting a conventional saline bag is attached to a side of the enclosure 32, as shown in FIG. 1. Additionally, medicines or other additives may be introduced into the blood through the access tubing 94 during treatment.

The reservoirs 46 and 64 and the manifold 51 of the blood handling cartridge 42, together with the tubes 38, 48, 52, 62 and 66, are collectively referred to as a blood tubing set ("BTS"). The BTS is disposable and is typically discarded after each dialysis treatment. Similarly, the dialyzer 54 is termed a disposable product, although it is not uncommon for a dialyzer to be reused with a single patient. A dialyzer will typically be reused by a patient who regularly visits the same clinic for dialysis treatments. Following each treatment, the dialyzer is cleaned with a sterilant and is then stored until the patient's next visit to the clinic. The dialyzer must then be thoroughly cleaned before use to ensure that the sterilant is not transferred to the patient's bloodstream during the next dialysis treatment.

Before each treatment, the disposable BTS and the dialyzer 54 (regardless of whether the dialyzer is new or "used") must be attached to a dialysis machine 30 and prepared for a patient's use by an operator. While the disposable BTS is sterile and thus does not need to be cleaned, the BTS and the dialyzer 54 must be primed with a sterile saline solution to remove the air from the extracorporeal circuit. In addition to flushing the dialyzer 54 with saline solution during priming, the saline solution must be recirculated through the dialyzer for a predetermined period of time to ensure that substantially all of the sterilant or other chemical debris within the dialyzer has been removed. This recirculation process also establishes a stable flow within the extracorporeal circuit and ensures that any remaining air within the circuit has been removed before the patient is connected to the machine 30. Once the priming and recirculating process is completed and the circuit is filled with saline, the arterial line 38 is attached to the patient and the patient's blood is drawn through the circuit. The venous line 66 is connected to the waste drain 86 to dispose of the used saline solution and, at the point the patient's blood has displaced all the saline within the circuit, the venous line is connected to the patient, as shown in FIG. 2.

The automatic nature of the present invention allows a dialysis machine operator to attach the BTS and the dialyzer 54 to the dialysis machine 30 and make a small number of other connections to the BTS prior to commanding the machine 30 to perform both the priming and the recirculation procedures discussed above. Upon the conclusion of the recirculation procedure, the machine 30 will place itself in a steady state mode and provide an indication that it is ready for connection to a patient.

Figure 3:
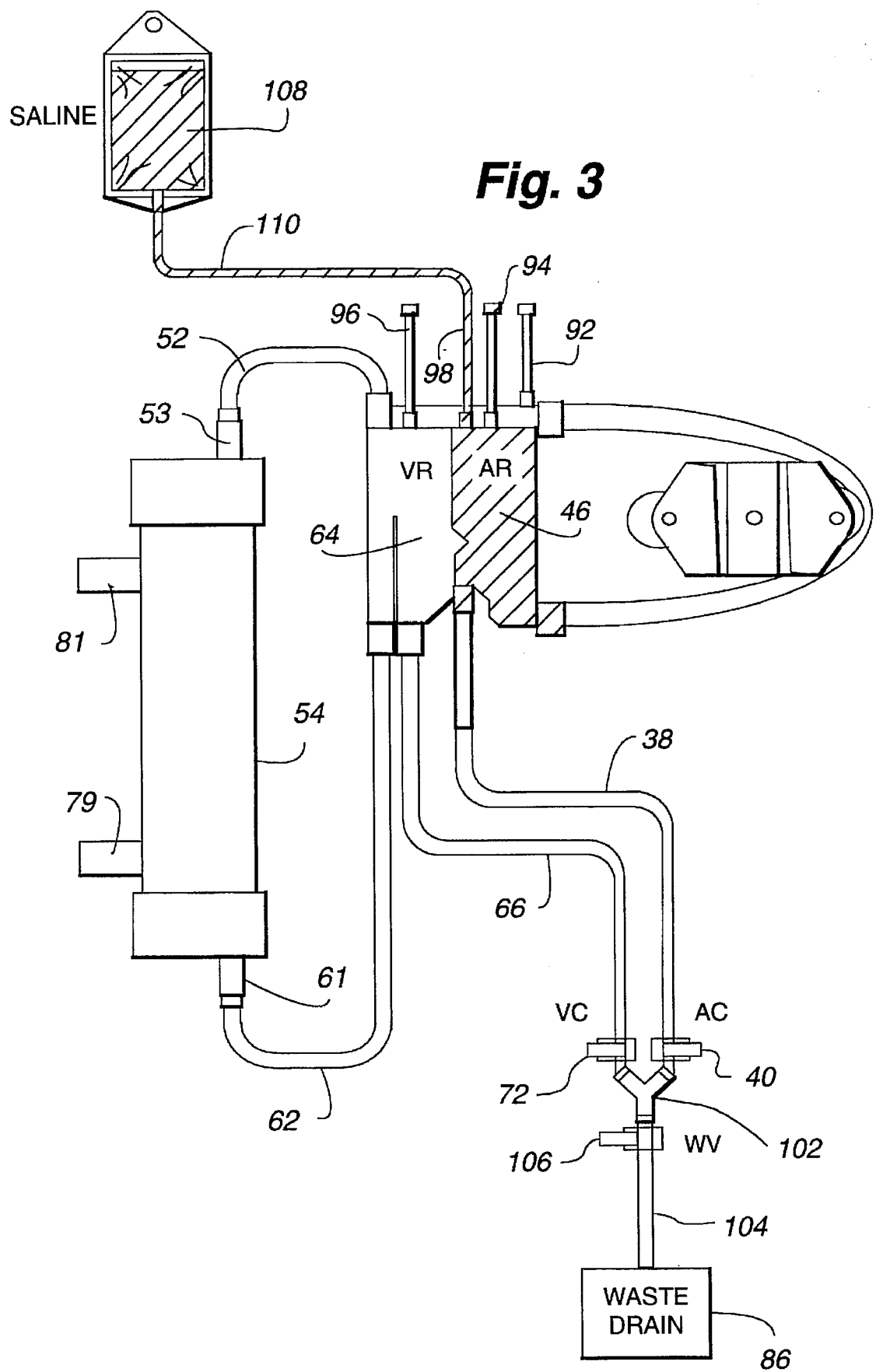
FIGS. 3–7 generally illustrate a dialyzer connected to a blood tubing set which together define the extracorporeal flow path shown in FIG. 2, each of FIGS. 3–7 showing a different stage within a priming and recirculating process which prepares the dialysis machine shown in FIG. 1 for use with a patient.

The present invention utilizes the known elements of the dialysis machine and the BTS mentioned above, together with two new components to achieve its automatic functionality. First, as shown in FIG. 3, the BTS includes a Y- or T-shaped connector 102 (FIG. 8) which is adapted to commonly connect the ends of the arterial line 38 and the venous line 66 to a waste line 104 which, in turn, is connected to the waste basin or drain 86. The waste line 104 is considered to be separate from the waste tubing 82 (FIG. 2) leading from the outlet 81 of the dialyzer 54, although one skilled in the art could utilize a single waste tubing for both purposes. Secondly, a waste valve 106 is used to selectively open and close the waste line 104. When the valve 106 is open, fluid within the Y-shaped connector 102 is directed to the waste drain 86. However, the valve 106 may be closed to effectively connect the arterial line 38 to the venous line 66 through the Y connector 102 when the arterial and venous clamps 40 and 72 are open.

Figure 8:
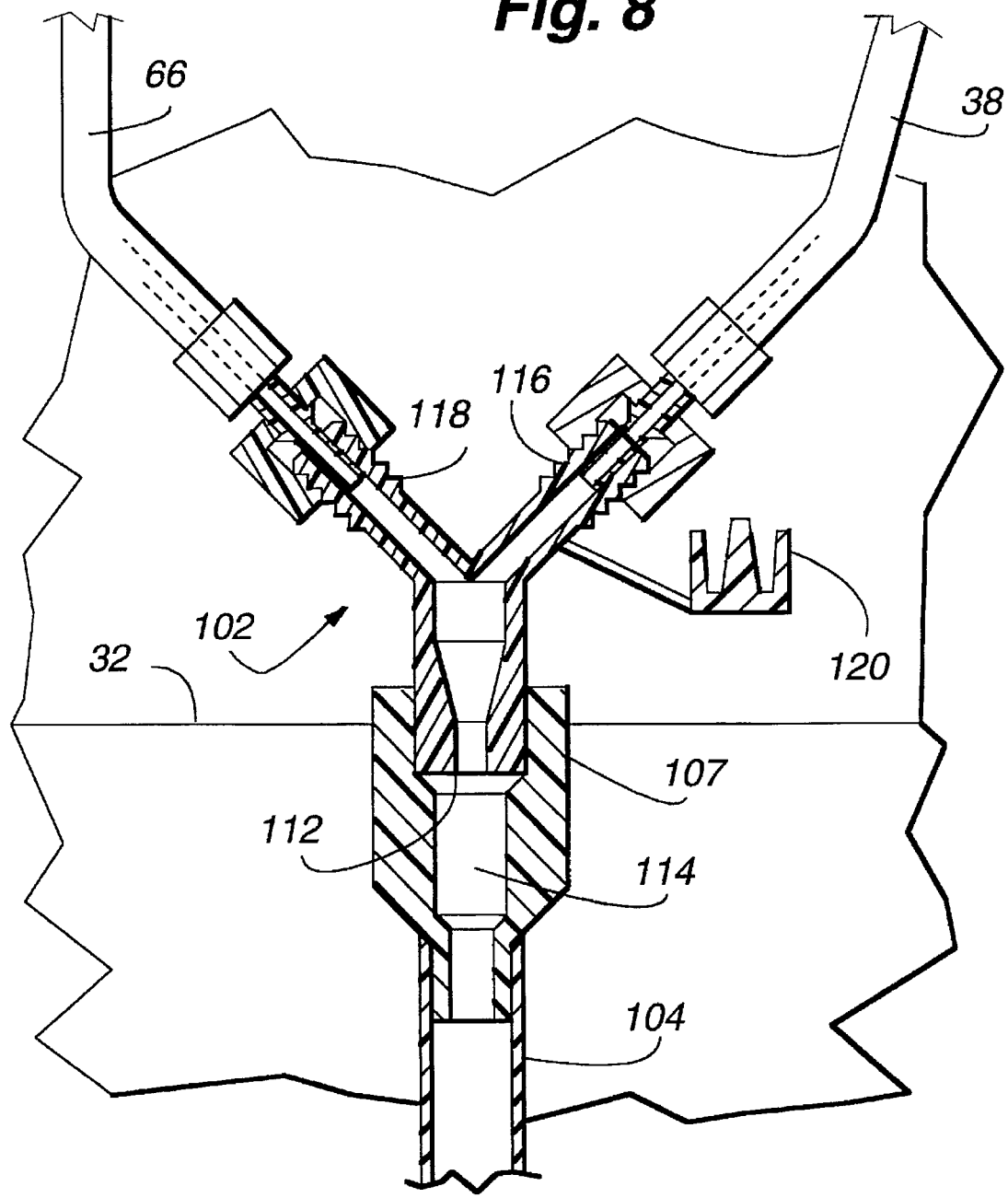
FIG. 8 is a generalized section view of a connector of the present invention connecting an arterial line and a venous line to a waste port on the dialysis machine shown in FIG. 1.

In an alternative preferred embodiment (FIG. 8), the waste valve 106 may be internal to the dialysis machine 30 so that an external waste handling port 107 may be used to connect the connector 102 to the waste drain 86. Details of such a waste handling port for use on a dialysis machine may be found in U.S. Pat. No. 5,041,215, entitled Dialysis Unit Priming and assigned to the assignee hereof, the disclosure of which is incorporated herein by this reference. When the waste handling port 107 is utilized, as shown in FIG. 8, a male portion 112 of the Y-shaped connector 102 is inserted directly within the port 107. The waste line 104 is connected to a bottom end of the port 107 and passes through the waste valve 106 (not shown in FIG. 8) which is internal to the dialysis machine enclosure 32. The port 107 preferably defines a relatively large gap 114 between the male portion 112 of the connector 102 and the waste line 104 to provide a sterile "air barrier" between the Y-shaped connector 102 and fluid within the waste line 104. The remaining two ends 116 and 118 of the Y-shaped connector 102 preferably include male Luer connectors for connection to the arterial and venous lines 38 and 66, respectively.

Although the Y-shaped connector 102 is preferably pre-attached to the arterial and venous lines 38 and 66 as shown in FIG. 8 (and may be pre-attached to the waste line 104 when the external waste valve 106 is used as shown in FIGS. 3–7), the Y-shaped connector may be packaged separately for attachment to blood tubing sets which do not include a Y-shaped connector. Additionally, while the waste port 107 and the internal waste valve 106 are preferably used as shown in FIG. 8, the waste valve 106 is illustrated with the waste drain 86 on the exterior of the dialysis machine in FIGS. 3–7 for the sake of clarity in describing the remainder of the invention.

Before the start of the priming process, the operator must attach the BTS (including the Y-shaped connector 102 and the attached waste line 104) and the dialyzer 54 to the dialysis machine 30 as shown in FIG. 1. The pump header 48 (FIG. 2) is placed about the pump rotor 49 and the tubings 52 and 62 are connected to the dialyzer 54, as shown in FIG. 3. Next, the operator must pass the lines 38 and 66 through their respective clamps 40 and 72, and connect the waste line 104 through the waste valve 106 to the waste drain 86.

After connecting the various lines as shown in FIG. 3 and ensuring that the clamps 40 and 72 are closed, the operator must hang a bag 108 of sterilized saline from the pole 100 (FIG. 1) and, after spiking the bag, connect a line 110 from the bag 108 to the saline tubing 98 on the arterial reservoir 46. The operator then opens the cap on the tubing 94 leading from the arterial reservoir 46, thus allowing saline from the bag 108 to gravity fill the arterial reservoir 46 as air within the reservoir 46 escapes through the tubing 94. Once the arterial reservoir 46 is mostly filled with saline (FIG. 3), the operator closes the cap on the tubing 94. The dialysis machine 30 is now set for priming and recirculation, and the operator's sole remaining task is to select the automatic prime and recirculate function from the touch screen 33 (FIG. 1).

Figure 4:
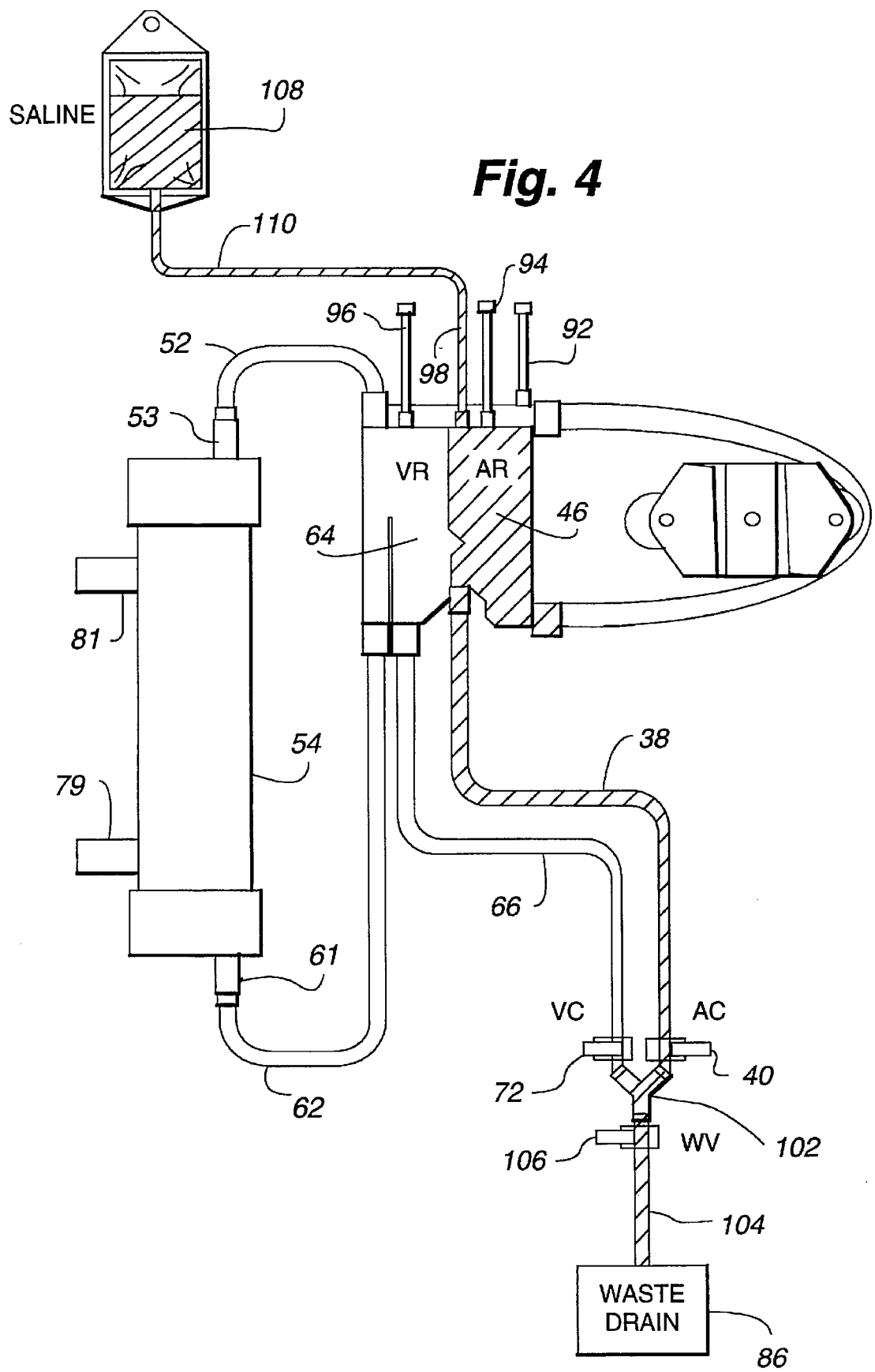

Once commanded to begin, the dialysis machine initiates the priming procedure, as shown in FIG. 4, by opening the arterial clamp 40 and the waste valve 106, thereby allowing the saline within the arterial reservoir 46 to flush the air out of the arterial line 38 before it is disposed of down the waste drain 86. The saline within the arterial reservoir 46 is replenished from saline within the bag 108, and the machine 30 closes the arterial clamp 40 after a predetermined time period to preserve the sterile saline solution within the bag 108. However, the predetermined time is sufficient to clear the air from the arterial line 38.

Figure 5:
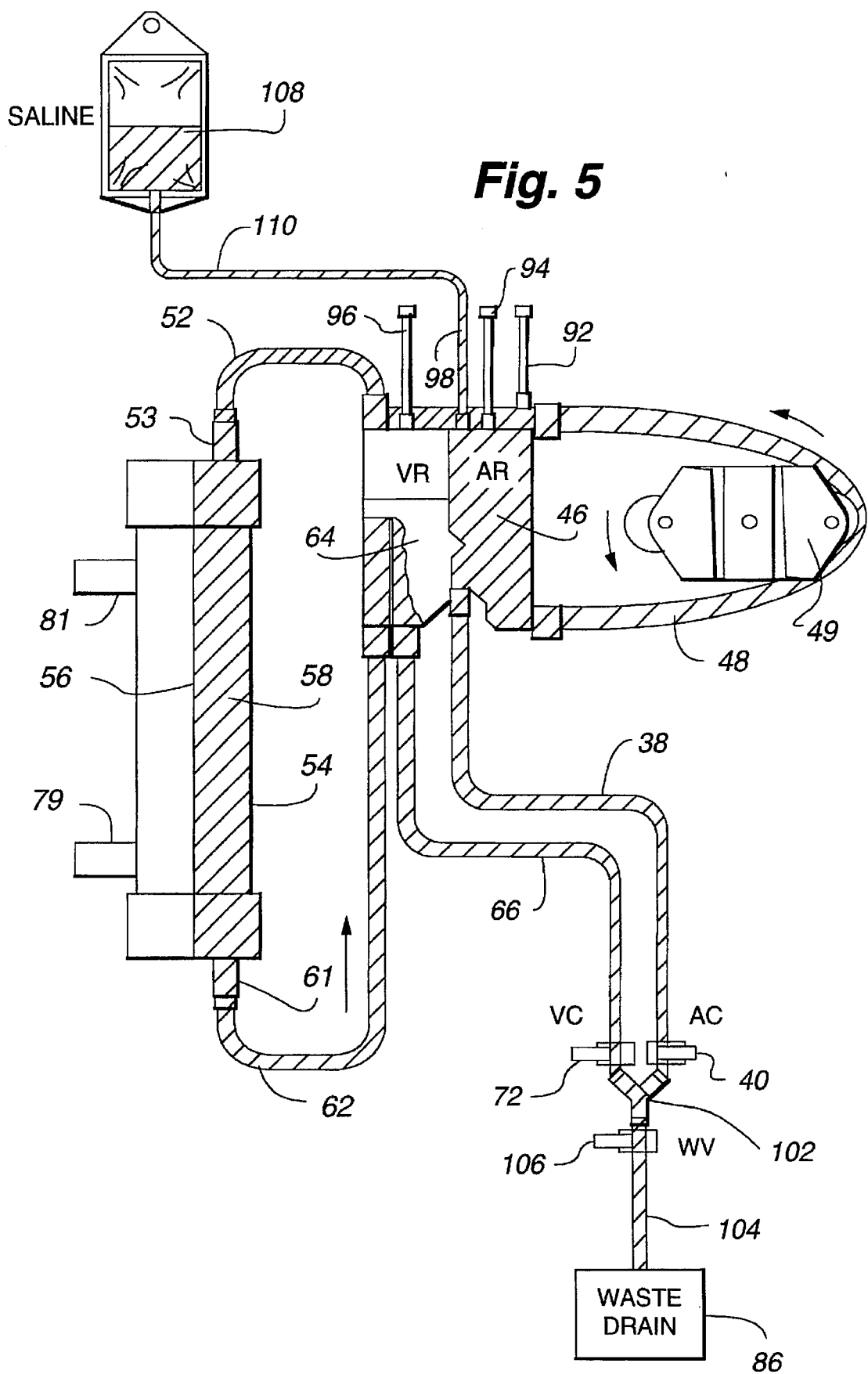

The machine 30 immediately initiates the next step in the automatic priming process, as shown in FIG. 5, by closing the arterial clamp 40 and opening the venous clamp 72. The machine then commands the pump rotor 49 to turn in a forward direction to fill the remainder of the extracorporeal circuit (the BTS and the dialyzer 54) with saline from the bag 108. The saline passes through the pump header 48, the manifold 51, the tubing 52, the dialyzer 54 and the tubing 62 before entering the venous reservoir 64. The saline then drains from the outlet 65 (FIG. 2) of the venous reservoir and through the venous line 66 (past the open venous clamp 72) and the Y-shaped connector 102 to the waste drain 86. During this step, additional saline is drawn from the bag 108 to maintain saline level within the arterial reservoir 46.

Priming the circuit in this manner serves to either flush a new dialyzer 54 (as is typically recommended by dialyzer manufacturers) or to cleanse a majority of the sterilant from a reused dialyzer. Additionally, a majority of the air within the BTS and the dialyzer 54 is expelled with the saline (and any sterilant flushed from the dialyzer) down the waste drain 86. However, some air will remain trapped within the dialyzer 54, and this trapped air typically floats to the top of the blood chamber 58 adjacent the inlet 53.

Figure 6:
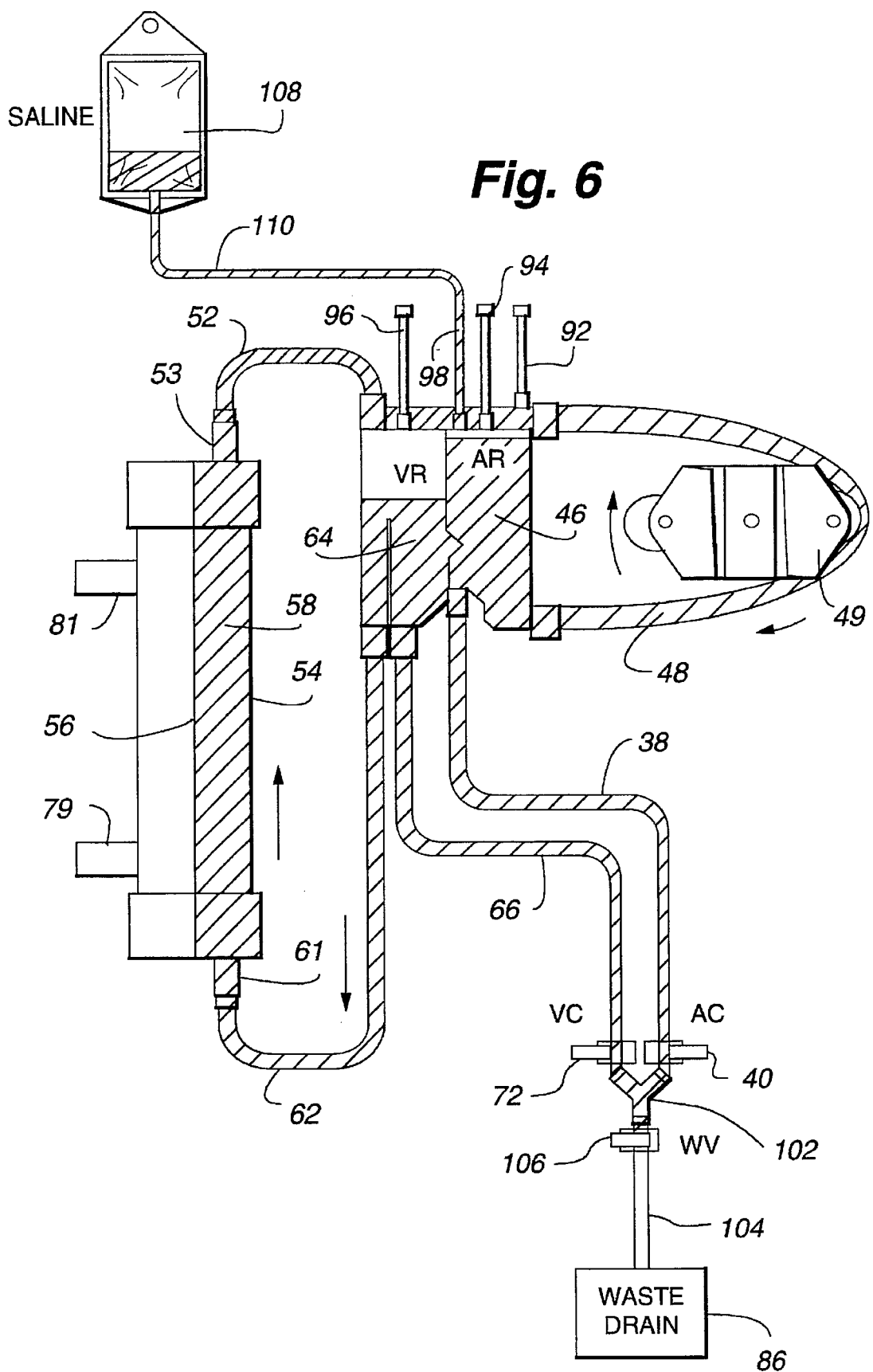
Figure 6A:
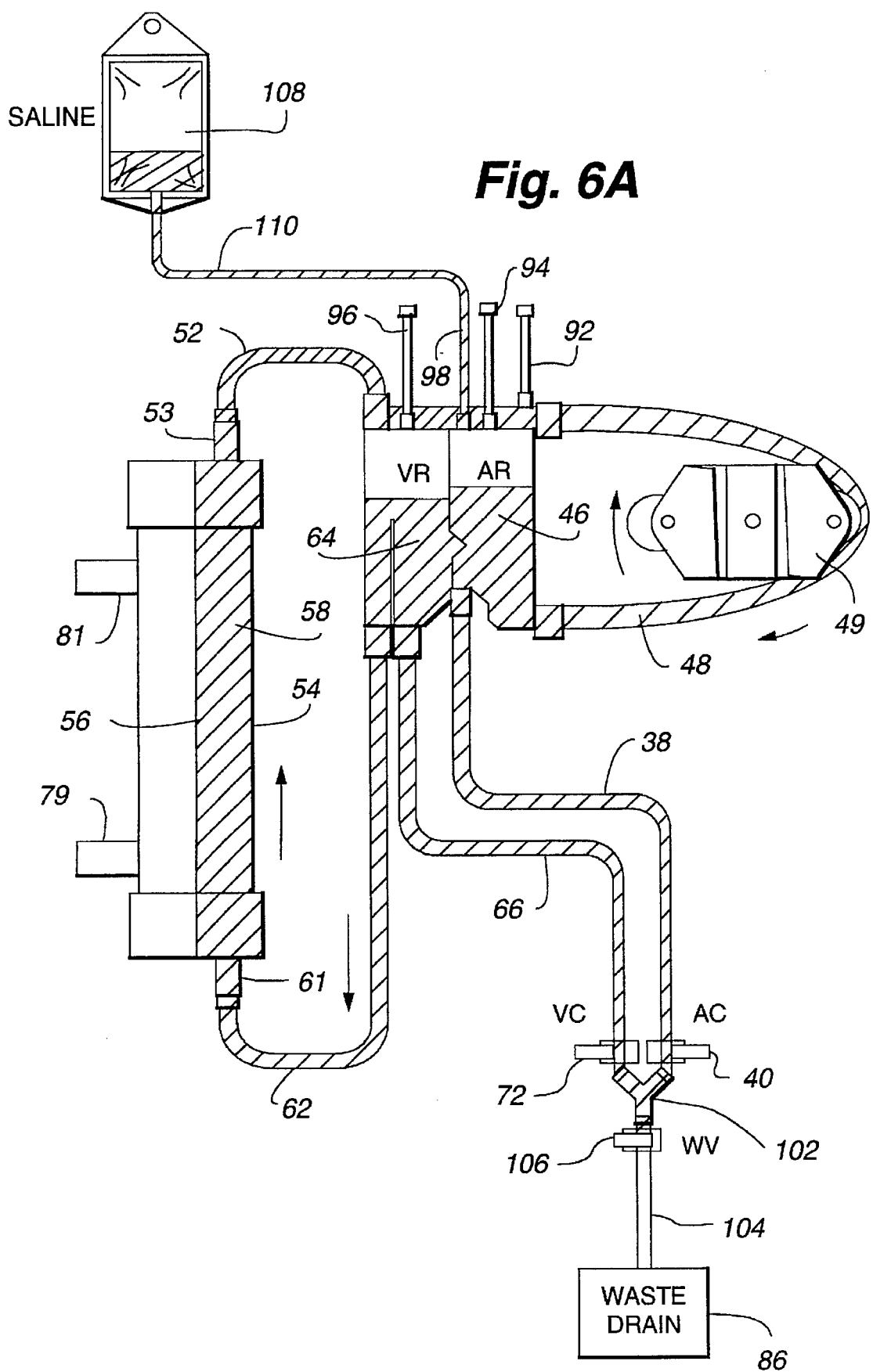

The next step in the automatic priming sequence, shown in FIG. 6, is to close the waste valve 106, open the arterial clamp 40, and run the blood pump rotor 49 backwards to push the saline solution backwards through the extracorporeal circuit. The fluid is pushed out of the arterial reservoir 46, through the Y-shaped connector 102, into the venous reservoir 64 and backward through the dialyzer 54 so that a portion of the air within the venous reservoir 64, together with the air trapped at the top of the dialyzer 54, is pushed out the inlet 53 and into the manifold 51. The entrained air bubbles are then forced by the pump 34 into the arterial reservoir 46 where they collect at the top of the reservoir. As more air bubbles are forced into the arterial reservoir 46, the increased air volume at the top of the reservoir reduces the level of saline in the arterial reservoir 46 while simultaneously preventing additional saline from entering the reservoir 46 through the saline tubing 98, as shown in FIG. 6A.

Figure 7:
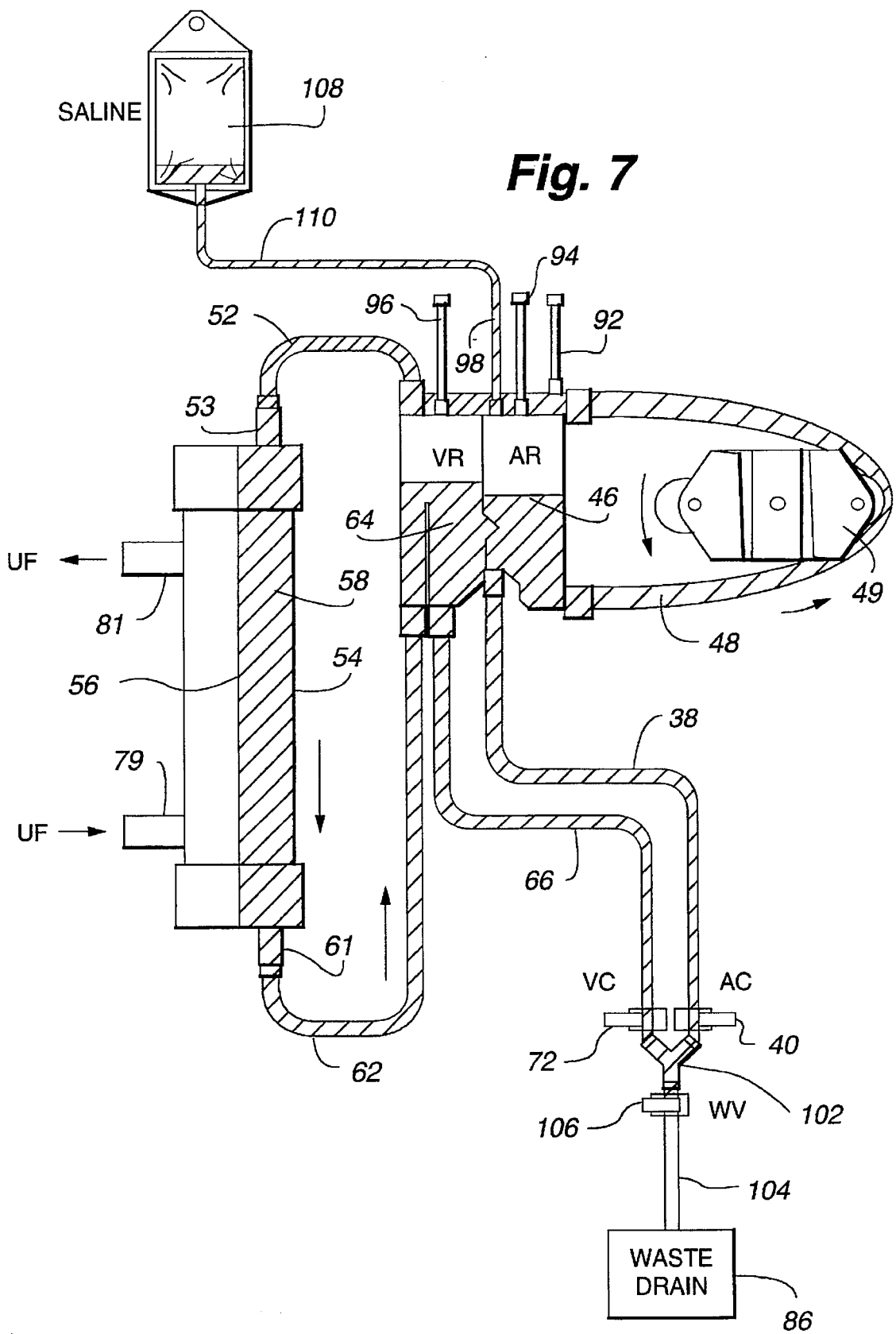

Once the air has been forced out of the BTS and the dialyzer 54, and the fluid levels in the reservoirs 64 and 46 have been adjusted, the machine 30 automatically switches from the priming procedure to the recirculation procedure without the need to reconfigure any of the connections of the dialyzer, the saline bag or the BTS. The recirculation procedure, as shown in FIG. 7, entails closing the waste valve 106, opening the arterial and venous clamps 40 and 72, and running the blood pump 34 forward while the machine 30 commands the hydraulics responsible for the dialysate flow path to pull a predetermined level of fluid from the dialyzer 54 across the medium 56.

In essence, the recirculation process mimics the normal dialysis process while short circuiting the patient 36 by connecting the arterial and venous lines 38 and 66, respectively, through the Y-shaped connector 102. By commanding the dialysate hydraulics to pull a certain amount of fluid from the blood chamber 58 of the dialyzer 54, the machine 30 is essentially conducting ultrafiltration. However, the liquid pulled through the medium 56 comprises only the saline solution and any sterilant still remaining within the dialyzer 54 following the priming procedure. The recirculation process thus helps to ensure that a reused dialyzer is properly cleansed before it is connected to a patient.

To prevent air from filling the extracorporeal circuit as saline is pulled from the dialyzer during recirculation, additional saline is gravity fed from the bag 108 into the arterial reservoir 46. The recirculation process also helps to collect any air remaining within either the dialyzer 54 or the BTS and deposit the air at the tops of both the venous and the arterial reservoirs 64 and 46. The air collected within these reservoirs can then be vented at the conclusion of the recirculation process by opening the clamps (not shown) on the tubes 96 and 94, respectively.

After a predetermined time during which the touch screen monitor 33 (FIG. 1) may provide a count-down timer to display the time remaining for recirculation, the machine 30 notifies the operator via an audible signal (in conjunction with an indication on the touch screen monitor 33) that the recirculation process has been completed. Simultaneously, the machine commands the dialysate hydraulics to stop pulling fluid through the dialyzer medium 56 and simply allows the pump to continue recirculating the saline through the extracorporeal circuit. By halting the "ultrafiltration" process, the machine 30 conserves the saline that must be drawn from the bag 108 to replenish the fluid pulled from the dialyzer.

Although no additional fluid is pulled from the extracorporeal circuit, the machine continues to recirculate the saline within the circuit until the patient is ready to be connected to the machine. In addition to maintaining an established flow, the continued recirculation helps to dilute any potential pockets of sterilant remaining within the dialyzer.

The operator thus knows when the machine 30 has finished both the priming and the recirculation procedures. The operator further knows that if the patient is delayed, the machine will continue its beneficial recirculation function while not wasting any saline once the machine has halted the ultrafiltration process. The clinic can thus set its parameters, including the predetermined times and fluid volumes used for each step of the priming and recirculating process, so that a sufficient level of saline remains within the bag 108 for use during the dialysis treatment. As noted above, the saline bag 108 is left attached to the saline tube 98 of the arterial reservoir 46 during patient treatment. Although the saline line 110 will normally be clamped during the dialysis treatment, the line 110 may be opened in case the patient experiences low blood pressure and requires an influx of fluid.

Once the priming and recirculation procedures are completed, the operator needs only to clamp the lines 94 and 110 and disconnect the arterial line 38 from the Y-shaped connector 102. A leashed cap 120 on the Y-shaped connector is placed over the end 116 to prevent saline within the BTS from spilling out of the Y-shaped connector 102 once the arterial line 38 is disconnected. The arterial line 38 is then attached to the patient 36, as shown in FIG. 2. As the patient's blood displaces the saline solution within the extracorporeal circuit, the venous line 66 remains connected to the waste drain 86 through the Y-shaped connector 102 to dispose of the recirculated saline. Once the patient's blood reaches the end of the venous line 66, the venous line is disconnected from the end 118 of the Y-shaped connector 102 and attached to the patient as shown in FIG. 2. The disposable Y-shaped connector 102 may then be discarded. The dialysis treatment thus progresses in a normal fashion from this point.

As noted above, the different steps of the automatic priming and recirculating process, as shown in FIGS. 4–7, require that the various clamps be opened and closed at specific predetermined times and that the pump rotor 49 be run in various directions and at various speeds for predetermined durations. A microprocessor (not shown) within the enclosure 32 is programmed to operate the clamps and pumps as described above to perform both the priming and the recirculation procedures. Thus, the different hospitals and clinics using the dialysis machine 30 need only program the microprocessor with the different predetermined times and durations (and their corresponding fluid volumes) according to a specific set of parameters previously established by the hospital or clinic. As an example only, and not by way of limitation, during the step in the automatic priming process shown in FIG. 4, the machine 30 may be programmed to open the arterial clamp 40 for 7 seconds to flush the arterial line 38 with the saline stored in the arterial reservoir 46. The clinic may have previously determined through testing that the 7 second period is sufficient to completely flush the air out of the arterial line 38, and that leaving the clamp 40 open for a longer period would only serve to waste the sterile saline solution. Similarly, the clinic will typically establish a parameter for the amount of time the blood pump 34 is to run in the recirculation step shown in FIG. 7 before the dialysate hydraulics are commanded to stop pulling fluid through the dialyzer medium (e.g., 20 minutes). Alternatively, the lengths of the different steps may be varied with different types of dialyzers. These predetermined times (and the corresponding predetermined volume of saline used) will have been established by the clinic to both ensure that a sufficient amount of time and saline solution is allowed to achieve the desired effect, and to prevent both time and saline solution from being wasted by extending the step for an excessive period of time.

Additionally, variations on a particular step may be programmed into the machine 30 to account for changing variables. For instance, as mentioned above, the step of priming the venous side of the circuit, including the dialyzer 54 (FIG. 5), can be altered when a new dialyzer is used. Dialyzer manufacturers typically require that a new dialyzer be flushed with saline for a longer period than a dialyzer which is being reused. Thus, when the machine 30 is informed that a new dialyzer is being used, it can prolong the step shown in FIG. 5 to meet the manufacturer's requirements. Similarly, if a plate dialyzer is utilized in place of the more typical hollow fiber dialyzers illustrated in FIGS. 1–7, the dialyzer manufacturer typically suggests that the dialyzer be subjected to a high pressure flow during priming to expand the plates within the dialyzer (similar to blowing up a balloon). If the machine 30 is informed that a plate dialyzer is being used, it may alter the above-described step of resetting the fluid level in the venous reservoir 64 by closing the venous clamp 72 for a longer period of time and allowing the pressure within the dialyzer to rise to a greater level before popping open the venous clamp 72.

Thus, the significant contribution of the present invention is that a clinic or hospital may be certain that their established parameters for setting up a dialysis machine are being precisely followed with no possibility of human error or distraction. Also, the machine 30 may be programmed for different contingencies, such as using different types of dialyzers. However, the greatest benefit of the present invention is that it allows busy nurses or dialysis operators the freedom to direct their attention elsewhere while the dialysis machine automatically cycles through the various steps of the priming and the recirculation procedures. The operator no longer has to revisit a dialysis machine and change the configuration of the blood tubing set over the course of the machine set-up. Rather, the operator is only required to make a limited number of connections before starting the procedure and then, after informing the machine of all the potential variable parameters (i.e., the type of dialyzer used), command the machine to start the procedure. The operator can then turn his or her attention to other patients or other machines requiring set up, comfortable in the knowledge that the dialysis machine will complete the priming and recirculation procedures according to the preestablished parameters and then notify the operator when it is ready to be connected to a patient. In clinical settings where large numbers of machines must be set up, the present invention can save a great deal of operator time, while simultaneously ensuring that each machine is being set up in a manner consistent with the clinic's established parameters. The labor savings associated with the present invention, together with the savings realized from using an optimum amount of saline during the priming and recirculation procedures, translates to a notable monetary savings to hospitals and dialysis clinics.

The technique of the present invention relates both to the novel method of priming and recirculating a dialysis machine and the unique apparatus which enables the machine to carry out the new method. This apparatus includes the waste valve 106 (not previously used on dialysis machines) and the Y-shaped connector 102 (not previously included with conventional blood tubing sets). Additionally, while a preferred embodiment of the present invention is illustrated with a double-needle dialysis treatment (i.e., using a single pump 34 to draw and return blood to the patient at two separate locations as shown in FIG. 2), one skilled in the art could apply the same technique to a dialysis machine which utilizes two separate blood pumps to both draw and return blood from a single location on the patient (i.e., "single-needle, double-pump" machines). As noted above, provision is made for the inclusion of a second blood pump (not shown) on the face of the enclosure 32 behind the door 68 (FIG. 1). Furthermore, while the presently preferred embodiment of the invention requires the dialysis operator to initially fill the arterial reservoir by unclamping and then clamping the air tubing 94 (FIG. 3), one skilled in the art would be able to automate this step in the priming and recirculating process similar to the remaining steps shown in FIGS. 4–7.

The present invention could be utilized with existing dialysis machines once they have been fitted with the waste valve 106 (and appropriate microprocessor software for controlling the blood pump and the valves), in addition to the arterial clamp 40 if the machine does not already include an arterial clamp (as is common with some single pump dialysis machines). Additionally, conventional blood tubing sets must be modified to include the Y-shaped connector 102. Thus, the present invention may be utilized with both new and existing dialysis machines which include the above-described apparatus.

A presently preferred embodiment of the present invention and many of its improvements have been described with a degree of particularity. This description is a preferred example of implementing the invention, and is not necessarily intended to limit the scope of the invention. The scope of the invention is defined by the following claims.

The invention claimed is:

1. A method of priming a dialysis machine having a pump, a dialyzer, and a blood tubing set which includes an arterial line for drawing blood from a patient, an arterial reservoir for storing the blood received from the patient, a venous reservoir for storing the blood pumped from the arterial reservoir through the dialyzer, and a venous line for returning the blood from the venous reservoir to the patient, said method comprising the steps of:

connecting the arterial line and the venous line to two arms of a connector;

connecting a third arm of the connector to a waste drain;

connecting a waste valve between the third arm of the connector and the waste drain;

closing an arterial clamp on the arterial line to prevent fluid from filling the arterial line;

filling the arterial reservoir with a sterile solution;

opening the arterial clamp and the waste valve to fill the arterial line with sterile solution from the arterial reservoir and to allow the sterile solution within the arterial line to drain through the connector and down the waste drain past the open waste valve;

closing the arterial clamp;

opening a venous clamp on the venous line and running the pump in a forward direction to draw sterile solution from the arterial reservoir through the dialyzer and the venous reservoir and allow the sterile solution to drain through the venous line and the connector and down the waste drain past the open waste valve;

closing the waste valve, opening the arterial clamp and running the pump backwards to draw the sterile solution backwards through the dialyzer and the blood tubing set; and running the pump forward to recirculate the sterile solution through the dialyzer and the blood tubing set.

2. A method as defined in claim 1 wherein the dialysis machine includes a microprocessor adapted to automatically operate the pump, the arterial clamp, the venous clamp and the waste valve, and wherein:

the steps following the step of filling the arterial reservoir with a sterile solution are performed automatically by the dialysis machine.

3. A method as defined in claim 1 wherein the dialysis machine includes a microprocessor adapted to automatically operate the pump, the arterial clamp, the venous clamp and the waste valve, and wherein:

the steps following the step of connecting a waste valve between the third arm of the connector and the waste drain are performed automatically by the dialysis machine.

4. A method as defined in claim 1 further comprising the step of replenishing the sterile solution within the dialyzer and the blood tubing set as the sterile solution is disposed of down the waste drain.

5. A method as defined in claim 1 further comprising the step of drawing fluid directly out of the dialyzer and disposing of the fluid during the step of recirculating the sterile solution through the dialyzer and the blood tubing set.

6. A method as defined in claim 5 further comprising the step of replenishing the sterile solution within the dialyzer and the blood tubing set when the sterile solution is either drained through the connector or drawn directly from the dialyzer and disposed of down the waste drain.

7. A method as defined in claim 6 wherein the dialysis machine includes a microprocessor adapted to automatically operate the pump, the arterial clamp, the venous clamp and the waste valve, and wherein:

the steps following the step of filling the arterial reservoir with a sterile solution are performed automatically by the dialysis machine.

8. A method as defined in claim 5 wherein the step of recirculating the sterile solution through the dialyzer and the blood tubing set continues until the dialysis machine is connected to the patient.

9. A method as defined in claim 8 wherein the step of drawing fluid directly from the dialyzer is halted at a predetermined time after the initiation of the step of recirculating the sterile solution through the dialyzer and the blood tubing set.

10. A method as defined in claim 9, further comprising the step of providing an indication that the dialysis machine is ready for connection to the patient at a point following the predetermined time when the step of drawing fluid directly from the dialyzer is halted.

11. A method as defined in claim 10 wherein the dialysis machine includes a microprocessor adapted to automatically operate the pump, the arterial clamp, the venous clamp and the waste valve, and wherein:

the steps following the step of filling the arterial reservoir with a sterile solution are performed automatically by the dialysis machine.

12. A method as defined in claim 1 wherein the step of running the pump in a forward direction to draw sterile solution through the dialyzer and down the waste drain is prolonged when a new dialyzer is used in conjunction with the blood tubing set as opposed to reusing a previously used dialyzer.

13. A method as defined in claim 1 wherein the dialyzer is a plate dialyzer having a plurality of plates separated from one another to define adjacent blood and dialysate channels within the dialyzer, and further comprising the steps of:

closing the venous clamp during the step of recirculating the sterile solution through the dialyzer and the blood tubing set to increase the fluid pressure within the dialyzer and separate the plates within the dialyzer from one another; and opening the venous clamp to equalize the pressure within the dialyzer and the blood tubing set after the plates within the plate dialyzer have been sufficiently separated.

14. A method as defined in claim 13 wherein the dialysis machine includes a microprocessor adapted to automatically operate the pump, the arterial clamp, the venous clamp and the waste valve, and wherein:

the steps following the step of filling the arterial reservoir with a sterile solution are performed automatically by the dialysis machine.

15. A method of priming a dialysis machine having a pump, a dialyzer, and a blood tubing set which includes an arterial line for drawing blood from a patient, a venous reservoir for storing the blood pumped from the arterial reservoir through the dialyzer, and a venous line for returning the blood from the venous reservoir to the patient, said method comprising the steps of:

connecting the arterial line and the venous line to two arms of a connector;

connecting a third arm of the connector to a waste drain;

connecting a waste valve between the third arm of the connector and the waste drain;

filling the arterial line with a sterile solution and opening the waste valve and an arterial clamp on the arterial line to allow the sterile solution within the arterial line to drain through the connector and down the waste drain past the open waste valve;

closing the arterial clamp;

opening a venous clamp on the venous line and running the pump in a forward direction to draw sterile solution from the arterial line through the dialyzer and the venous reservoir and allow the sterile solution to drain through the venous line and the connector and down the waste drain past the open waste valve; and closing the waste valve, opening the arterial clamp and running the pump to recirculate the sterile solution through the dialyzer and the blood tubing set.

16. A method as defined in claim 15 wherein the dialysis machine includes a microprocessor adapted to automatically operate the pump, the arterial clamp, the venous clamp and the waste valve, and wherein:

the steps following the step of filling the arterial line with a sterile solution and opening the waste valve and the arterial clamp are performed automatically by the dialysis machine.

17. A method as defined in claim 15 wherein the dialysis machine includes a microprocessor adapted to automatically operate the pump, the arterial clamp, the venous clamp and the waste valve, and wherein:

the steps following the step of connecting a waste valve between the third arm of the connector and the waste drain are performed automatically by the dialysis machine.

18. A method as defined in claim 15 further comprising the step of replenishing the sterile solution within the dialyzer and the blood tubing set as the sterile solution is disposed of down the waste drain.

19. A method as defined in claim 15 further comprising the step of drawing fluid directly out of the dialyzer and disposing of the fluid during the step of recirculating the sterile solution through the dialyzer and the blood tubing set.

20. A method as defined in claim 19 wherein the step of recirculating the sterile solution through the dialyzer and the blood tubing set continues until the dialysis machine is connected to the patient.

21. A method as defined in claim 20 wherein the step of drawing fluid directly from the dialyzer is halted at a predetermined time after the initiation of the step of recirculating the sterile solution through the dialyzer and the blood tubing set.

22. A method as defined in claim 21, further comprising the step of providing an indication that the dialysis machine is ready for connection to the patient at a point following the predetermined time when the step of drawing fluid directly from the dialyzer is halted.

23. A method as defined in claim 22 wherein the dialysis machine includes a microprocessor adapted to automatically operate the pump, the arterial clamp, the venous clamp and the waste valve, and wherein:

the steps following the step of filling the arterial line with a sterile solution and opening the waste valve and the arterial clamp are performed automatically by the dialysis machine.

24. A method as defined in claim 15 wherein the step of running the pump in a forward direction to draw sterile solution through the dialyzer and down the waste drain is prolonged when a new dialyzer is used in conjunction with the blood tubing set as opposed to reusing a previously used dialyzer.

25. A method as defined in claim 15 wherein the dialyzer is a plate dialyzer having a plurality of plates separated from one another to define adjacent blood and dialysate channels within the dialyzer, and further comprising the steps of:

closing the venous clamp during the step of recirculating the sterile solution through the dialyzer and the blood tubing set to increase the fluid pressure within the dialyzer and separate the plates within the dialyzer from one another; and opening the venous clamp to equalize the pressure within the dialyzer and the blood tubing set after the plates within the plate dialyzer have been sufficiently separated.

26. A method as defined in claim 25 wherein the dialysis machine includes a microprocessor adapted to automatically operate the pump, the arterial clamp, the venous clamp and the waste valve, and wherein:

the steps following the step of filling the arterial line with a sterile solution and opening the waste valve and the arterial clamp are performed automatically by the dialysis machine.

27. A method as defined in claim 15 wherein the step of recirculating the sterile solution through the dialyzer and the blood tubing set continues until the dialysis machine is connected to the patient.

28. A method of priming a dialysis machine having a pump, a dialyzer, and a blood tubing set which includes an arterial line for drawing blood from a patient, a pump header for pumping the blood to the dialyzer, and a venous line for returning the blood pumped through the dialyzer to the patient, said method comprising the steps of:

connecting the arterial line and the venous line to two arms of a connector;

connecting a third arm of the connector to a waste drain;

connecting a waste valve between the third arm of the connector and the waste drain;

filling the arterial line with a sterile solution and opening the waste valve and an arterial clamp on the arterial line to allow the sterile solution within the arterial line to drain through the connector and down the waste drain past the open waste valve;

closing the arterial clamp;

opening a venous clamp on the venous line and running the pump in a forward direction to draw sterile solution from the arterial line through the pump header and the dialyzer and allow the sterile solution to drain through the venous line and the connector and down the waste drain past the open waste valve; and closing the waste valve, opening the arterial clamp and running the pump to recirculate the sterile solution through the dialyzer and the blood tubing set.

29. A method as defined in claim 28 wherein the dialysis machine includes a microprocessor adapted to automatically operate the pump, the arterial clamp, the venous clamp and the waste valve, and wherein:

the steps following the step of filling the arterial line with a sterile solution and opening the waste valve and the arterial clamp are performed automatically by the dialysis machine.

30. A method as defined in claim 28 further comprising the step of drawing fluid directly out of the dialyzer and disposing of the fluid during the step of recirculating the sterile solution through the dialyzer and the blood tubing set.

31. A method as defined in claim 30 wherein the step of drawing fluid directly from the dialyzer is halted at a predetermined time after the initiation of the step of recirculating the sterile solution through the dialyzer and the blood tubing set.

* * * * *